US008548841B1

(12) United States Patent
Hiller et al.

(10) Patent No.: US 8,548,841 B1
(45) Date of Patent: Oct. 1, 2013

(54) SUPPLY EXPENSE ANALYSIS

(75) Inventors: Mark Edward Hiller, Cornelius, NC (US); Eugene A. Kroch, Swarthmore, PA (US); Melisa Junco Paulik, Charlotte, NC (US)

(73) Assignee: Premier Healthcare Solutions, Inc., Charlotte, NC (US)

( * ) Notice: Subject to any disclaimer, the term of this patent is extended or adjusted under 35 U.S.C. 154(b) by 236 days.

(21) Appl. No.: 12/892,897

(22) Filed: Sep. 28, 2010

Related U.S. Application Data

(60) Provisional application No. 61/246,785, filed on Sep. 29, 2009.

(51) Int. Cl.
*G06Q 10/00* (2012.01)
*G06Q 50/00* (2012.01)

(52) U.S. Cl.
USPC .................. 705/7.39; 705/2; 705/3

(58) Field of Classification Search
USPC ................................ 705/2–3, 7.39
See application file for complete search history.

(56) References Cited

U.S. PATENT DOCUMENTS

| 2003/0167198 A1* | 9/2003 | Northcott et al. ............... 705/10 |
| 2010/0274580 A1* | 10/2010 | Crownover et al. ............. 705/2 |
| 2011/0196719 A1* | 8/2011 | Bhandari et al. ............. 705/7.39 |

OTHER PUBLICATIONS

Weiyan Jian1, Yinmin Huang1, Mu Hu2 and Xiumei Zhang3; "Performance evaluation of inpatient service in Beijing: a horizontal comparison with risk adjustment based on Diagnosis Related Groups"; Published Apr. 30, 2009; Accessed Aug. 12, 2012; http://www.biomedcentral.com/1472-6963/9/72.*

* cited by examiner

*Primary Examiner* — Lena Najarian
*Assistant Examiner* — Minnah Seoh
(74) *Attorney, Agent, or Firm* — McDermott Will & Emery LLP

(57) ABSTRACT

A method for comparing a hospital's existing supply expenses to another hospital's existing supply expenses is described. The method includes determining a number of patient cases ($C_i$) associated with each diagnosis related classification ($DRC_i$) from a plurality of DRCis, receiving a supply mix index weight ($SMI_i$) value for each $DRC_i$ from the plurality of $DRC_i$s, and determining, with a processor, a weighted supply mix index value for each of the plurality of $DRC_i$s based on the $SMI_i$ value for each $DRC_i$ and the $C_i$ for the corresponding $DRC_i$. The method also includes determining an overall HCP supply mix index ($HCP_{SMI}$) for the hospital based on the sum of the weighted supply mix index value for each of the plurality of $DRC_i$s and the sum of $C_i$ for each of the plurality of $DRC_i$s, and outputting the $HCP_{SMI}$ for the hospital. Other methods, systems, and machine-readable media are also described.

11 Claims, 7 Drawing Sheets

| | Provider 21 | HCP 140 22 | Patient 150 23 | Disch_Date 24 | LOS 25 | M_S_Flag 26 | MDC 27 | DRC 28 | Central Supply Identifier 29 | Central Supply Cost 30 | DME Identifier 31 | DME Cost 32 |
|---|---|---|---|---|---|---|---|---|---|---|---|---|
| 1 | | | | | | | | | | | | |
| 2 | ABC1 | Hospital A | 123 | 2007-11-26 | 2 | MED | 06 | 386 | 0 | $0 | 0 | $0 |
| 3 | ABC1 | Hospital A | 124 | 2007-11-26 | 3 | MED | 05 | 287 | 270 | $185 | 0 | $0 |
| 4 | ABC1 | Hospital A | 125 | 2007-11-26 | 13 | SURG | 05 | 234 | 270 | $5,404 | 290 | $34 |
| 5 | ABC1 | Hospital A | 126 | 2007-11-26 | 6 | SURG | 05 | 236 | 270 | $4,740 | 0 | $0 |
| 6 | ABC1 | Hospital A | 127 | 2007-11-26 | 7 | SURG | 01 | 24 | 270 | $4,973 | 290 | $9 |
| 7 | ABC1 | Hospital A | 128 | 2007-11-26 | 6 | SURG | 05 | 234 | 270 | $4,178 | 0 | $0 |
| 8 | ABC1 | Hospital A | 129 | 2007-11-26 | 5 | MED | 06 | 379 | 270 | $5 | 0 | $0 |
| 9 | ABC1 | Hospital A | 130 | 2007-11-26 | 5 | MED | 11 | 690 | 270 | $7 | 0 | $0 |
| 10 | XYZ1 | Hospital B | 100 | 2007-11-26 | 4 | MED | 06 | 378 | 270 | $5 | 0 | $0 |
| 11 | XYZ1 | Hospital B | 101 | 2007-11-26 | 3 | MED | 08 | 556 | 270 | $39 | 0 | $0 |
| 12 | XYZ1 | Hospital B | 102 | 2007-11-26 | 2 | MED | 08 | 555 | 270 | $11 | 0 | $0 |
| 13 | XYZ1 | Hospital B | 103 | 2007-11-26 | 10 | MED | 01 | 69 | 270 | $117 | 0 | $0 |
| 14 | XYZ1 | Hospital B | 104 | 2007-11-26 | 8 | MED | 18 | 870 | 270 | $201 | 0 | $0 |
| 15 | XYZ1 | Hospital B | 105 | 2007-11-26 | 3 | MED | 05 | 310 | 0 | $0 | 0 | $0 |
| 16 | XYZ1 | Hospital B | 106 | 2007-11-26 | 3 | MED | 06 | 392 | 0 | $0 | 0 | $0 |
| 17 | XYZ1 | Hospital B | 107 | 2007-11-26 | 15 | SURG | 01 | 29 | 0 | $0 | 0 | $0 |
| 18 | XYZ1 | Hospital B | 108 | 2007-11-26 | 19 | SURG | 01 | 21 | 270 | $9,537 | 290 | $0 |
| 19 | XYZ1 | Hospital B | 109 | 2007-11-26 | 2 | MED | 05 | 313 | 270 | $0 | 0 | $0 |
| 20 | XYZ1 | Hospital B | 110 | 2007-11-26 | 7 | SURG | 05 | 234 | 270 | $4,923 | 0 | $0 |

FIG. 2

| Pharmacy Identifier | Pharmacy Cost | CB + Pharma + DME Cost | DRC Aug_TH_Cost | Cost Over_ 2-Std_Dev | Cost=0 |
|---|---|---|---|---|---|
| 33 | 34 | 35 | 36 | 37 | 38 |
| 250 | $337 | $337 | $1,352 | FALSE | FALSE |
| 250 | $427 | $612 | $1,127 | FALSE | FALSE |
| 250 | $3,143 | $8,581 | $8,578 | FALSE | FALSE |
| 250 | $1,067 | $5,807 | $7,443 | FALSE | FALSE |
| 250 | $2,284 | $7,266 | $7,842 | FALSE | FALSE |
| 250 | $1,295 | $5,473 | $8,578 | FALSE | FALSE |
| 250 | $733 | $738 | $522 | FALSE | FALSE |
| 250 | $468 | $475 | $669 | FALSE | FALSE |
| 250 | $196 | $201 | $828 | FALSE | FALSE |
| 250 | $247 | $286 | $480 | FALSE | FALSE |
| 250 | $336 | $347 | $946 | FALSE | FALSE |
| 250 | $1,020 | $1,137 | $372 | FALSE | FALSE |
| 250 | $3,097 | $3,298 | $9,376 | FALSE | FALSE |
| 250 | $582 | $582 | $406 | FALSE | FALSE |
| 250 | $220 | $220 | $623 | FALSE | FALSE |
| 250 | $1,050 | $1,050 | $9,263 | FALSE | FALSE |
| 250 | $3,934 | $13,480 | $18,129 | FALSE | FALSE |
| 250 | $423 | $423 | $347 | FALSE | FALSE |
| 250 | $1,468 | $6,391 | $8,578 | FALSE | FALSE |

*FIG. 2*
*(Continued)*

Supply Mix Index (SMI)

An Example of Results – Hospital A vs. Hospital B

Hospital A (15 day LOS):
- Avg supply cost = $644
- CMI = 0.7740
- Avg supply cost / CMI = $831

Hospital B (LOS 4):
- Avg supply cost = $9,592
- CMI = 2.3228
- Avg supply cost / CMI = $4,129

*CMI results => Hosp A => lower adjusted cost (20% of Hosp B)*

- SMI = 0.1816
- Avg supply cost / SMI = $3,543

- SMI = 4.4852
- Avg supply cost / SMI = $2,139

*SMI results => Hosp B => lower adjusted cost (60% of Hosp A)*

FIG. 5

SUPPLY EXPENSE ANALYSIS

CROSS-REFERENCE TO RELATED APPLICATIONS

The present application claims the benefit of priority under 35 U.S.C. §119 from U.S. Provisional Patent Application Ser. No. 61/246,785 entitled "SUPPLY MIX INDEX," filed on Sep. 29, 2009, the disclosure of which is hereby incorporated by reference in its entirety for all purposes.

BACKGROUND

1. Field

This disclosure is directed to managing health care resources. More particularly, the disclosure is directed to normalizing and comparing healthcare provider supply expenses.

2. Description of the Related Art

Supply costs are increasingly scrutinized as overall operating costs rise for healthcare providers (HCPs). The supply costs can include the sum of all purchases of patient supplies, surgical supplies, general medical supplies, laboratory supplies, linens, office supplies, and the like. These costs may constitute a significant percentage of total operating costs for a HCP. Accordingly, a number of metrics have been instituted to measure HCP supply costs. For example, supply costs are frequently measured as a percentage of revenue of total expenses, percentage of adjusted patient days (e.g., the total gross revenue divided by total inpatient revenue multiplied by the number of patient days), or per adjusted discharge. While such metrics may provide information on a particular HCP's performance with respect to supply spending, the metrics provide little, if any, information regarding the HCP's supply costs as compared to other HCPs, because the metrics assume that the types of patients the HCP serves are relatively the same.

External benchmarking methods, such as Case Mix Index (CMI), are commonly used to adjust for patient mix differences between HCPs, such as hospitals. For instance, CMI is calculated by averaging a Diagnosis Related Group (DRG) (or Medicare Severity DRG, MS-DRG) weighting for all patients served over a predetermined calculating period. In this regard, all patients are coded with a DRG, or MS-DRG that represents the resource consumption requirements based on, e.g., a patient's diagnosis, a patient's treatment, a patient's age, a patient's sex, a procedure performed on the patient, and the like.

However, external benchmarking methods like CMI are frequently inadequate to accurately predict supply expenses, or to "normalize" the supply expenses of HCPs to allow for accurate evaluation of resource management by the HCP or comparison to the resource management of other HCPs.

SUMMARY

In certain embodiments, a method for comparing a hospital's existing supply expenses to another hospital's existing supply expenses is provided. The method includes receiving a supply cost ($SC_i$) associated with each patient case from among a plurality of patient cases, wherein each patient case is associated with at least one diagnosis related classification ($DRC_i$) from a plurality of DRCis. The method also includes determining, with a processor, an average supply cost value ($AVG\text{-}SC_i$) associated with each of the plurality of $DRC_i$s based on the $SC_i$ associated with each patient case associated with each of the plurality of $DRC_i$s and the number of patient cases ($C_i$) associated with each of the corresponding plurality of $DRC_i$s. The method further includes determining an overall average supply cost value ($SC_{Avg}$) for each patient case based on the $SC_i$ associated with each patient case and Ci, determining a supply mix index weight ($SMI_i$) value for each $DRC_i$ based on $AVG\text{-}SC_{Avg}$ associated with each of the plurality of $DRC_i$s and the $SC_{Avg}$ for each patient case, and outputting the $SMI_i$ result.

In certain embodiments, a method for comparing a hospital's existing supply expenses to another hospital's existing supply expenses is provided. The method includes determining a number of patient cases ($C_i$) associated with each diagnosis related classification ($DRC_i$) from a plurality of DRCis, receiving a supply mix index weight ($SMI_i$) value for each $DRC_i$ from the plurality of $DRC_i$s, and determining, with a processor, a weighted supply mix index value for each of the plurality of $DRC_i$s based on the $SMI_i$ value for each $DRC_i$ and the $C_i$ for the corresponding $DRC_i$. The method also includes determining an overall HCP supply mix index ($HCP_{SMI}$) for the hospital based on the sum of the weighted supply mix index value for each of the plurality of $DRC_i$s and the sum of $C_i$ for each of the plurality of $DRC_i$s, and outputting the $HCP_{SMI}$ for the hospital.

In certain embodiments, a system for comparing a hospital's existing supply expenses to another hospital's existing supply expenses is provided. The system includes a memory for storing at least a supply cost ($SC_i$) associated with each patient case from among a plurality of patient cases, wherein each patient case is associated with at least one diagnosis related classification ($DRC_i$) from a plurality of $DRC_i$s. The system also includes a processor configured to determine an average supply cost value ($AVG\text{-}SC_i$) associated with each of the plurality of $DRC_i$s based on the $SC_i$ associated with each patient case associated with each of the plurality of $DRC_i$s and the number of patient cases ($C_i$) associated with each of the corresponding plurality of $DRC_i$s, to determine an overall average supply cost value ($SC_{Avg}$) for each patient case based on the $SC_i$ associated with each patient case and $C_i$, to determine a supply mix index weight ($SMI_i$) value for each $DRC_i$ based on $AVG\text{-}SC_{Avg}$ associated with each of the plurality of $DRC_i$s and the $SC_{Avg}$ for each patient case, and to output the $SMI_i$ result.

In certain embodiments, a system for comparing a hospital's existing supply expenses to another hospital's existing supply expenses is provided. The system includes a memory for storing at least a supply mix index weight ($SMI_i$) value for each diagnosis related classification ($DRC_i$) from a plurality of $DRC_i$s. The system also includes a processor configured to determine a number of patient cases ($C_i$) associated with each $DRC_i$ from the plurality of $DRC_i$s, to determine a weighted supply mix index value for each of the plurality of $DRC_i$s based on the $SMI_i$ value for each $DRC_i$ and the $C_i$ for the corresponding $DRC_i$, to determine an overall HCP supply mix index ($HCP_{SMI}$) for the hospital based on the sum of the weighted supply mix index value for each of the plurality of $DRC_i$s and the sum of $C_i$ for each of the plurality of $DRC_i$s, and to output the $HCP_{SMI}$ result for the hospital.

In certain embodiments, a machine-readable medium comprising machine-readable instructions for causing a processor to execute a method for comparing a hospital's existing supply expenses to another hospital's existing supply expenses is provided. The method includes receiving a supply cost ($SC_i$) associated with each patient case from among a plurality of patient cases, wherein each patient case is associated with at least one diagnosis related classification ($DRC_i$) from a plurality of $DRC_i$s. The method also includes determining, with a processor, an average supply cost value ($AVG\text{-}SC_i$) associated with each of the plurality of $DRC_i$s based on the $SC_i$ associated with each patient case associated with each of the plurality of $DRC_i$s and the number of patient cases ($C_i$) associated with each of the corresponding plurality of $DRC_i$s. The method further includes determining an overall average supply cost value ($SC_{Avg}$) for each patient case based on the $SC_i$ associated with each patient case and $C_i$, determining a supply mix index weight ($SMI_i$) value for each $DRC_i$ based on AVG-$SC_{Avg}$ associated with each of the plurality of $DRC_i$s and the $SC_{Avg}$ for each patient case, and outputting the $SMI_i$ result.

In certain embodiments, a machine-readable medium comprising machine-readable instructions for causing a processor to execute a method for comparing a hospital's existing supply expenses to another hospital's existing supply expenses is provided. The method includes determining a number of patient cases ($C_i$) associated with each diagnosis related classification ($DRC_i$) from a plurality of DRCis, receiving a supply mix index weight ($SMI_i$) value for each $DRC_i$ from the plurality of $DRC_i$s, and determining, with a processor, a weighted supply mix index value for each of the plurality of $DRC_i$s based on the $SMI_i$ value for each $DRC_i$ and the $C_i$ for the corresponding $DRC_i$. The method also includes determining an overall HCP supply mix index ($HCP_{SMI}$) for the hospital based on the sum of the weighted supply mix index value for each of the plurality of $DRC_i$s and the sum of $C_i$ for each of the plurality of $DRC_i$s, and outputting the $HCP_{SMI}$ for the hospital.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 2 shows exemplary patient records that are extracted by the advisor system (or a database) of FIG. 1 from the patient data stored in the database.

FIG. 5 shows an exemplary comparison of HCPs Hospital A and Orthopedic Hospital using both a supply mix index calculation according to certain embodiments of the disclosure and a CMI calculation.

DETAILED DESCRIPTION

In the following detailed description, numerous specific details are set forth to provide a full understanding of the present disclosure. It will be obvious, however, to one ordinarily skilled in the art that the embodiments of the present disclosure may be practiced without some of these specific details. In other instances, well-known structures and techniques have not been shown in detail not to obscure the disclosure.

Healthcare providers, which may include, for example, hospitals, clinics, laboratories, or the like, are under ever-increasing pressure to keep costs down, while maintaining or improving the quality of care provided to patients. The supply chain can provide substantial opportunities for reducing costs and improving efficiencies. Generally, supply expenses make up a considerable part of a healthcare provider's spending. The present disclosure provides a method and system for accurately normalizing health care supply expenses to create benchmarks against which individual (or groups of) healthcare providers can be compared and evaluated in terms of, e.g., resource management. The present disclosure also provides a method and system for accurately comparing and/or evaluating the resource management performance of the individual (or groups of) healthcare providers to that of other healthcare providers.

The disclosure further provides a computer readable medium that embodies a computer program, which when executed on a general purpose computer, causes the computer to perform the method for accurately normalizing health care supply expenses to create benchmarks against which individual (or groups of) healthcare providers can be compared and evaluated in terms of, e.g., resource management, as well as a method for accurately comparing and/or evaluating the resource management performance of the individual (or groups of) healthcare providers to that of other healthcare providers.

Figure 1:
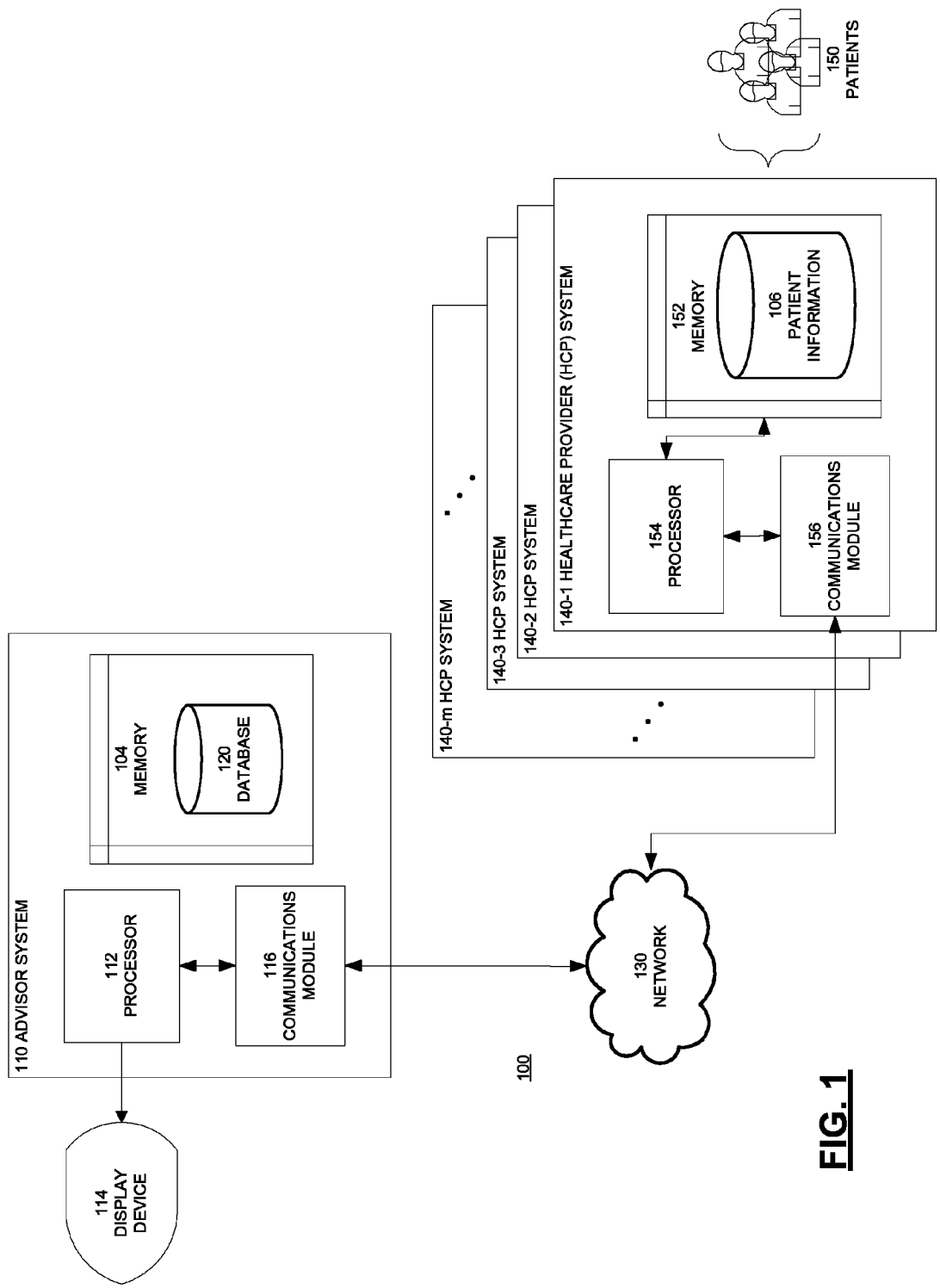
FIG. 1 illustrates an exemplary architecture of a system for normalizing health care supply expenses to create benchmarks against which HCPs may be compared and evaluated in terms of resource management, according to certain embodiments of the disclosure.

FIG. 1 illustrates an exemplary architecture 100 of a system 110 for normalizing health care supply expenses to create benchmarks against which healthcare provider systems 140 (e.g., each system associated with a healthcare provider) can be compared and evaluated in terms of, e.g., resource management. The architecture 100 comprises an advisor system 110 and one or more healthcare provider systems 140 connected via a network 130.

The advisor system 110, which can be, for example, a computer, includes a processor 112, communications module 116, display device 114, and memory 104 that includes a database 120. The advisor system 110 can include any combination of software or hardware, as the skilled artisan will readily recognize, including at least one application and/or at least one computer to perform services for connected clients as part of a client-server architecture. The advisor system 110 is configured to accept connections to service requests from other systems by sending back responses to the systems. The advisor system 110 can be configured to run the at least one application, often under heavy workloads, unattended, for extended periods of time with minimal human direction. The advisor system 110 can include a plurality of computers with software processing responsibilities being divided among the computers depending upon the workload. For example, under light loading, the software can run on a single computer. However, under heavy loading, multiple computers can be required to run the software. The advisor system 110, or any if its computers, can also be used as a workstation.

The database 120 of the advisor system 110 is configured to store and manage vast quantities of information, including a large number of patient records (e.g., thousands, millions, billions, or the like), thereby providing a significant population basis. The database 120 can include, for example, any combination of software or hardware configured to receive, organize, store, manage, or process data, including patient records, according to a database model, such as, for example but not limited to, a relational model, a hierarchical model, a network model, a post-relational model, an object model, or the like. The database 120 can further include a database management system (DBMS) to organize, store and manage the received data, including the patient records, as well as manage performance, concurrency, integrity, recovery from hardware failures, or the like.

The advisor system 110 is coupled by the communications module 116 (e.g., a modem or Ethernet card) to respective communications modules 156 of one or a plurality of HCP systems 140-1 to 140-m over the network 130. The network 130 can include, for example, any one or more of a personal area network (PAN), a local area network (LAN), a campus area network (CAN), a metropolitan area network (MAN), a wide area network (WAN), a broadband network (BBN), the Internet, or the like. Further, the network 130 can include, but is not limited to, for example, any one or more of the following network topologies, including a bus network, a star network, a ring network, a mesh network, a star-bus network, tree or hierarchical network, or the like.

Each HCP system 140, which can be a server, includes a communications module 156, processor 154, and memory 152 that includes patient records 106 for patients 150 associated with the HCP. The patients 150 can include persons or animals. Each of the one or more HCP systems 140-1 to 140-m can be associated with, for example, a hospital, a doctor's office, a laboratory, a clinic, an educational institution, other types of HCPs, either one or many, or the like, without limitation.

The processor 112 of the advisor system 110 is configured to retrieve patient data for one or all of the HCP systems 140-1 to 140-m from the database 120 (or, alternatively, from the patient information 106 stored in the HCP servers 140-1 to 140-m), as well as forward patient data to the database 120 for storage. In certain embodiments, the patient data is stored in the database 120 as a plurality of patient records, wherein each record can be associated with a unique patient 150.

FIG. 2 shows exemplary patient records 20 that are extracted by the advisor system 110 of FIG. 1 from the patient data stored in the database 120. As seen, each patient record (C) includes a plurality of fields, including, but not limited to, e.g., a patient identification field 23 (e.g., a name, a social security number, a patient key, a number, or the like), a healthcare provider (HPC) 140 identification fields 21, 22 (e.g., an HCP identifier, a name, a number, or the like) of the HPC 140 that provides (or provided) the care to the patient 150, a discharge date field 24, a length of stay (LOS) field 25, a Medical/Surgery flag field 26, a major diagnostic category (MDC) field 27, a diagnosis related classification (DRC) field 28, a central supply (CS) identifier field 29, a central supply (CS) cost field 30, a durable medical equipment (DME) identifier field 31, a durable medical equipment (DME) cost field 32, a pharmacy identifier field 33, a pharmacy cost field 34, a supply cost (or sum of the CS, DME and pharmacy costs) field 35, a DRC average total cost field 36, a cost over standard deviation field 37, a cost less than zero field 38, and the like. It is noted that the supply cost field 35 is not limited to the sum of the CS, DME and pharmacy costs, but, instead, in certain embodiments, includes any other expenses associated with a particular DRC for a particular patient 150. In certain embodiments, each patient record further includes a list of the charges associated with the DRC (or DRCs, where a particular patient record includes data for more than one DRC) for the particular patient 150.

In certain embodiments, the DRC includes, for example, but is not limited to, a Diagnosis Related Group (DRG), a Medicare Severity Diagnosis Related Group (MS-DRG), an All Patient Refined Diagnosis Related Group (APR™-DRG), or any other methodology for classifying patients and/or expenses related to patients on the basis of the patient's condition for which care and/or supplies can be provided by the HCP system 140. Any number of $DRC_i$ categories can be defined based on, e.g., the range of uniquely recognized patient 150 conditions for which individualized care and/or supplies can be provided by the HCP system 140, where i is a positive, non-zero integer ranging from 1 to a maximum number of defined classifications. For example, if the $DRC_i$ includes the seven-hundred-forty-six (746) MS-DRG categories defined by the Centers for Medicare and Medicaid Services, then the value i can range from 1 to 746, but in no way is the DRC limited to the MS-DRG categories defined by the Centers for Medicare and Medicaid Services.

Returning to FIG. 1, the patient data stored in the database 120 of the advisor system 110 in certain embodiments is searchable and/or accessible based any one or more of the plurality of fields 21-38 of FIG. 2. The processor 112 of the advisor system 110 is further configured to query the database 120 and receive the patient records 20 from the database 120, including the DRC data 28 and the associated supply cost data 35. The processor 112 in certain embodiments receives all, or a subset of all of the patient records 20 stored in the database 120. Alternatively, the processor 112 in certain embodiments queries the database 120 and receive the DRC data 28, associated supply cost data 35 and HCP identification data 21 (or 22) extracted from each of the patient records 20 in the database 120.

The processor 112 of the advisor system 110 is configured to extract the supply cost data 35 from each of the received patient records 20 (e.g., column 35 of FIG. 2) for all HCPs (e.g., HCP systems 140-1 to 140-m). On the basis of the extracted supply cost data 35, the processor 112 determines an average supply cost ($SC_i$) value for each available $DRC_i$ ($6,815 for DRC 234 for Hospitals A and B of FIG. 2) by summing all of the supply costs for each particular $DRC_i$ (e.g., $20,445 for DRC 234 of FIG. 2) and dividing the sum by the number of patient records (or cases) (e.g., 3 patient records in FIG. 2, namely rows 4, 7, and 20) associated with the particular $DRC_i$ (i.e., the number of records from which the supply cost data was extracted for the particular $DRC_i$). The processor 112 is also configured to sum all of the supply costs $SC_i$ extracted from the received patient records (e.g., $56,704 in FIG. 2) and divide the result by the total number of patient records (e.g., 19 patient records in FIG. 2) to determine an overall average supply cost per patient record (or case) (e.g., $2984.42 in FIG. 2). Based on the average supply cost ($SC_i$) value for each available $DRC_i$, and the overall average supply cost per patient, the processor 112 of the advisor system 110 determines a supply mix index ($SMI_i$) weight for each associated $DRC_i$ (e.g., to output/display on display device 114, such as a monitor or printer) by dividing the average supply cost ($SC_i$) value for each $DRC_i$ by the overall average supply cost per patient (e.g., 2.28 for DRC 234 for Hospitals A and B of FIG. 2). The processor 112 in certain embodiments then stores the average supply cost ($SC_i$) values, the overall average supply cost per patient value, and the supply mix index ($SMI_i$) weights for each associated $DRC_i$, locally in memory 104 and/or remotely in the database 120.

The processor 112 of the advisor system 110 is further configured to compare and evaluate the resource management performance of a particular HCP system (e.g., HCP system 140-1, associated with a particular HCP, Hospital A). In certain embodiments, this is done by determining a supply mix index ($HCP_{SMI}$) for the particular HCP system based on the volume of patients belonging to each $DRC_i$ in the HCP system 140-1 weighted by the $SMI_i$ weights for each of the $DRC_i$ in the HCP system 140-1. The $HCP_{SMI}$ for the HCP system 140-1 in certain embodiments is compared to the $HCP_{SMI}$ for each of the HCPs 140-2 to 140-m, or an aggregate $HCP_{SMI}$ for the entire group of HCPs 140-2 to 140-m, or any subset thereof, where m is a positive integer greater than 1. The resultant determination in certain embodiments is used to determine the efficiency and/or effectiveness of any one or more of the HCPs 140-1 to 140-m in, managing resources.

Figure 3:
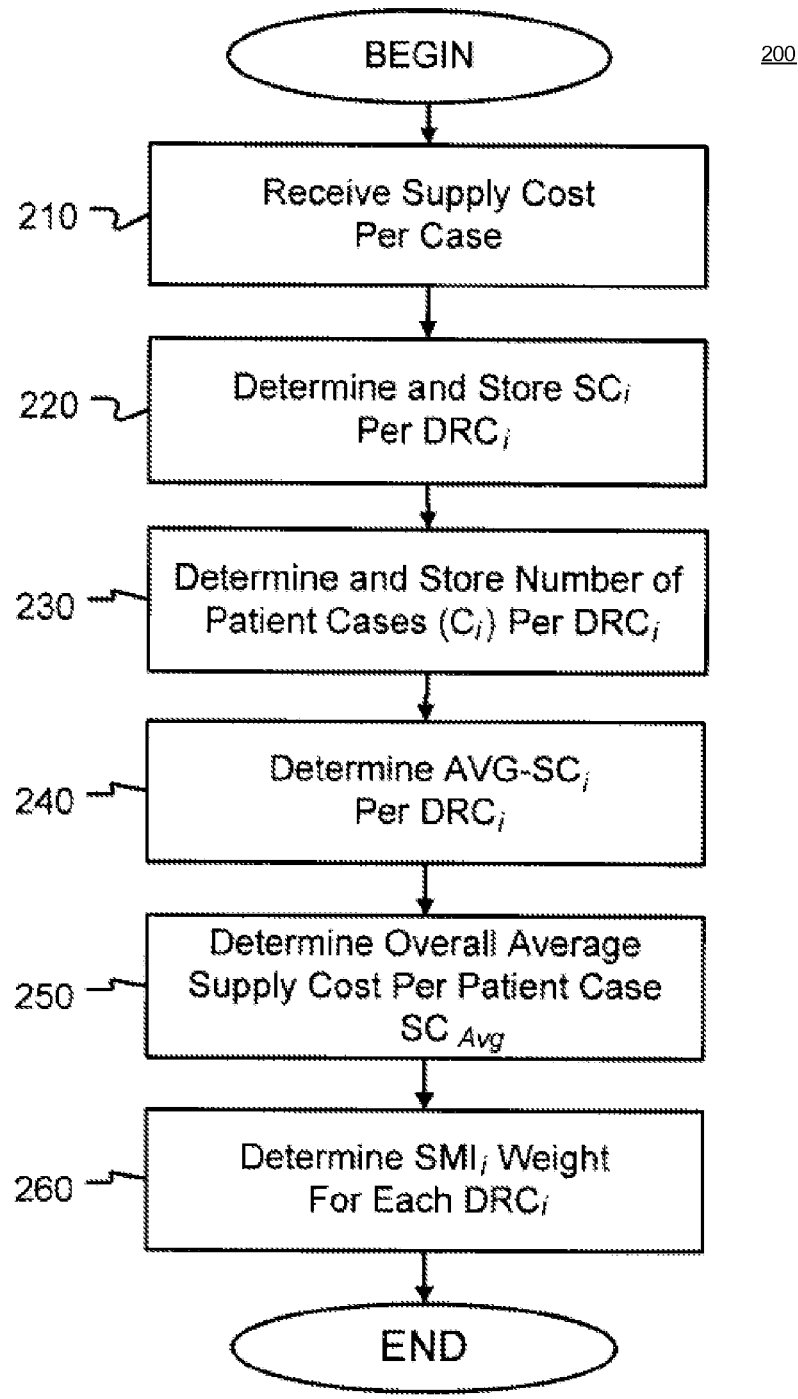
FIG. 3 shows an exemplary process for determining a supply mix index ($SMI_i$) weight for each of a plurality of $DRC_i$ according to certain embodiments of the disclosure.

FIG. 3 shows an exemplary process 200 for determining a supply mix index ($SMI_i$) weight for each of a plurality of $DRC_i$ according to certain embodiments of the disclosure. For illustrative purposes only, the process 200 is described below with regard to an HCP system 140-3 that comprises a hospital having two kinds of cases, knee replacements (e.g., $DRC_1$) and psychosis (e.g., $DRC_2$). The HCP system 140-3 comprises 100 inpatients for knee replacements ($DRC_1$) and 50 inpatients for psychosis ($DRC_2$). Further, the database 120 comprises, e.g., ten million patient records containing, e.g., 1,000 DRCs (i.e., $DRC_1$, $DRC_2$ ... $DRC_{1000}$).

Referring to FIGS. 1-3, the advisor system 110 queries the database 120 and receives (from the database 120) the following information for each patient record 20 stored in the database 120: a total supply cost 35 associated with a particular $DRC_i$, a DRC identification 28 for the particular $DRC_i$, and an HCP identification 22 (or 21) for the HCP system 140 that provided care for the particular $DRC_i$ (Step 210). Alternatively (or additionally), the advisor system 110 in certain embodiments receives all (e.g., ten million), or any subset of all (e.g., less than ten million) of the patient records 20 stored in the database 120 in response to the query.

Based on the received supply cost data 35 associated with each $DRC_i$ (e.g., $DRC_1$, $DRC_2$ ... $DRC_{1000}$) for each patient record 20 (or case), the advisor system 110 determines an average supply cost ($SC_i$) value for each of the $DRC_i$ by, e.g., summing all of the supply costs for each particular $DRC_i$ and dividing the sum by the number of patient records (or cases) associated with the particular $DRC_i$ (Step 220). The advisor 120 in certain embodiments stores the determined average supply cost values $SC_i$ (e.g., $SC_1$, $SC_2$ ... $SC_{1000}$) for each of the available $DRC_i$, (e.g., $DRC_1$, $DRC_2$ ... $DRC_{1000}$) (Step 220), such as in memory 104.

Also based on the received supply cost data 35 associated with each particular $DRC_i$ the advisor system 110 determines the number of patient cases ($C_i$) for each associated $DRC_i$ (e.g., $C_1$, $C_2$ ... $C_{1000}$) (Step 230). The advisor system 110 in certain embodiments stores each of the determined number of patient cases ($C_1$, $C_2$ ... $C_{1000}$) in memory 104, such as in the database 120 (Step 230).

The advisor system 110 determines an average supply cost value per $DRC_i$ ($AVG$-$SC_i$) by dividing each supply cost value $SC_i$ ($SC_1$, $SC_2$ ... $SC_{1000}$) by each associated number of patient cases $C_i$ ($C_1$, $C_2$ ... $C_{1000}$) (Step 240). The advisor system 110 in certain embodiments stores each of the average supply cost values $AVG$-$SC_i$ (e.g., $AVG$-$SC_1$, $AVG$-$SC_2$ ... $AVG$-$SC_{1000}$) in memory 104, such as in the database 120 (Step 240).

Next, the advisor system 110 determines the overall average supply cost value ($SC_{Avg}$) per patient case by summing all of the patient level supply cost values ($SC_{Total}$=$SC_1$+$SC_2$+ ... +$SC_{1000}$) and dividing the result ($SC_{Total}$) by the total number of patient cases ($C_{Total}$=$C_1$+$C_2$+ ... +$C_{1000}$) (Step 250). The advisor system 110 in certain embodiments stores the overall average supply cost value $SC_{Avg}$ per patient case in memory 104, such as in database 120 (Step 250).

Dividing each average supply cost value $AVG$-$SC_i$ (e.g., $AVG$-$SC_1$, $AVG$-$SC_2$ ... $AVG$-$SC_{1000}$) by the overall average supply cost value ($SC_{Avg}$) per patient, the advisor system 110 determines the supply mix index weight ($SMI_i$) value for each $DRC_i$ (e.g., $SMI_1$, $SMI_2$ ... $SMI_{1000}$) (Step 260). The advisor system 110 in certain embodiments stores each of the supply mix index weights $SMI_i$ ($SMI_1$, $SMI_2$ ... $SMI_{1000}$) in the local storage, or database 120 (Step 260).

A computer readable medium is provided that embodies a computer program, which, when executed on a general purpose computer in the advisor system 110, causes the computer to determine the supply mix index ($SMI_i$) weights for each of the plurality of $DRC_i$ categories. The computer program can include a code section (or segment) for each of the steps in FIG. 3, including, e.g., an extractor code section that extracts a supply cost per case for each patient; an average supply cost determiner code section that determines an average supply cost ($SC_i$) per $DRC_i$ category for all DRC categories; a patient case number determiner code section that determines the number of patient cases ($C_i$) for each associated $DRC_i$; an average supply cost value per $DRC_i$ determiner code section that determines the average supply cost value per $DRC_i$ ($AVG$-$SC_i$); an overall average supply cost value determiner code section that determines the overall average supply cost value ($SC_{Avg}$) per patient case; a supply mix index weight determiner code section that determines the supply mix index weight ($SMI_i$) value for each $DRC_i$.

Figure 4:
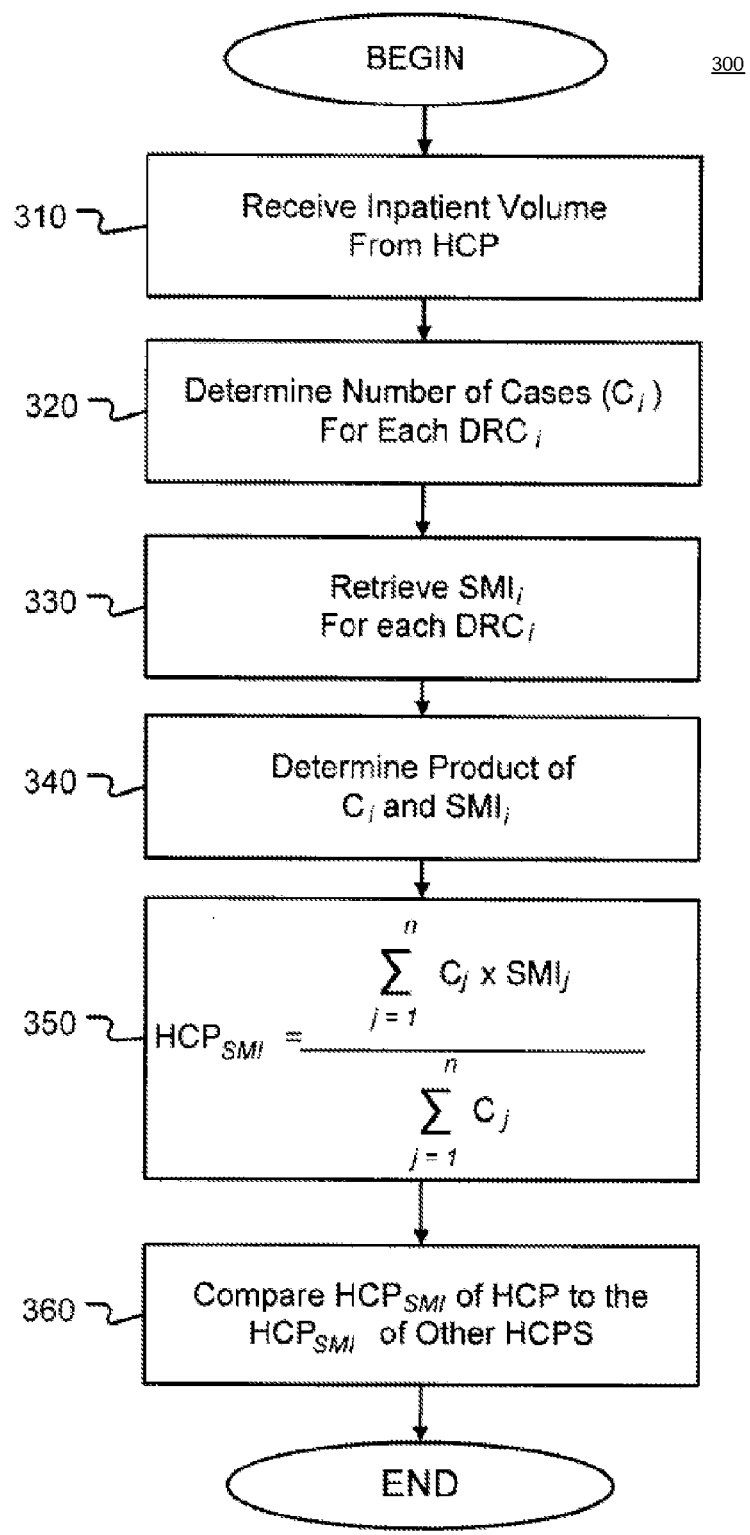
FIG. 4 shows an exemplary process for determining an overall HCP supply mix index ($HCP_{SMI}$) for a particular HCP and comparing resource management performance of the HCP to that of other HCPs according to certain embodiments of the disclosure.

FIG. 4 shows an exemplary process 300 for determining an overall HCP supply mix index ($HCP_{SMI}$) for a particular HCP system 140 and comparing (or evaluating) the resource management performance of the HCP system 140 (e.g., 140-3) to that of the other HCPs 140 (e.g., 140-1, 140-2, 140-4 to 140-m) according to certain embodiments of the disclosure. As noted earlier, for illustrative purposes only, the process is described below with regard to an HCP system 140-1 that comprises a hospital having two kinds of cases, knee replacements ($DRC_1$) and psychosis ($DRC_2$), where the HCP system 140-1 comprises 100 inpatients for knee replacements ($DRC_1$) and 50 inpatients for psychosis.

Referring to FIGS. 1 and 4, the advisor system 110 receives inpatient volume information from the HCP system 140-1 (Step 310). The received inpatient volume information in certain embodiments includes a $DRC_i$ category identifier (e.g., $DRC_i$ identification data) for each inpatient. Based on the received inpatient volume information (100 $DRC_1$, 50 $DRC_2$), the number of cases ($C_i$) for each $DRC_i$ category in certain embodiments is determined ($C_1$=100, $C_2$=50) (Step 320). In the above illustrative example, from the received inpatient volume information from the HCP system 140-1, in certain embodiments it is determined that the inpatient volume includes 150 cases, of which 100 cases ($C_1$) are associated with the $DRC_1$ category and 50 cases ($C_2$) are associated with the $DRC_2$ category.

Based on the $DRC_i$ categories of the inpatient volume cases in the HCP system 140-1, associated supply mix index ($SMI_i$) weights in certain embodiments are retrieved from the database 120 (or elsewhere in the memory 104 of the advisor system 110) (Step 330). Again, referring to the above illustrative example, supply mix indexes $SMI_1$ (=0.1124) and $SMI_2$ (=0.32) in certain embodiments are retrieved from memory 104, such as from the database 120.

Next, a product of the number of cases $C_i$ of each $DRC_i$ category and the associated supply mix index $SMI_i$ weights (i.e., $C_i \times SMI_i$) in certain embodiments are calculated to determine a weighted supply mix index value for each $DRC_i$ category (Step 340). Referring again to the above example, the weighted supply mix index values for HCP system 140-1 in certain embodiments are determined by multiplying $C_1$ by $SMI_1$, and multiplying $C_2$ by $SMI_2$, resulting in 100 $SMI_1$ (=11.24) and 50 $SMI_2$ (=16), where the sum of $SMI_1$ and $SMI_2$ has a value of less than 1.0 (i.e., 0.4234).

In step 350 of FIG. 4, an overall HCP supply mix index ($HCP_{SMI}$) in certain embodiments is determined for a particular HCP system 140 by summing the products of each of the number of cases $C_j$ with the associated supply mix index weight $SMI_j$ and dividing the result by the total number of cases in the HCP system 140 (=50) (i.e., $(\Sigma C_j \times SMI_j)/(\Sigma C_j)$, where j is a subset of i and can range from 1 to n, where n can equal a maximum possible value for i). Referring again to the above example, for the HCP system 140-1, the $HCP_{SMI}$ in certain embodiments is determined by summing the products 100 $SMI_1$ and 50 $SMI_2$ (=11.24+16=27.24) and dividing the result by the total number of cases 150 in HCP system 140-1 (=27.24/150=0.1816).

The HCP supply mix index ($HCP_{SMI}$) for, e.g., HCP system 140-1, in certain embodiments is compared to that of other HCPS 140-2 to 140-$m$, to determine whether the HCP system 140-1 is performing better than, or worse than various benchmark groups based on the mix of patient cases in HCP system 140-1 (Step 360). The benchmark groups in certain embodiments includes all, or a subset of HCP systems 140 that are regarded as performing optimally. That is, the $HCP_{SMI}$ for a particular HCP system 140 in certain embodiments is compared to the $HCP_{SMI}$ of all other HCPS 140 for which patient data is provided and/or stored in the database 120, or any subset thereof. For example, the $HCP_{SMI}$ for HCP system 140-1 in certain embodiments is compared to the $HCP_{SMI}$ for any one or more of HCP system 140-2 to 140-$m$. For instance, the $HCP_{SMI}$ for HCP system 140-1 in certain embodiments is compared to the $HCP_{SMI}$ for all HCPs specializing in orthopedic care, or any other specialty area. A particular subset of HCPS 140-1 to 140-$m$ in certain embodiments is selected based on any DRC-related criteria, such as, e.g., HCPs specializing in any health care area—e.g., cardiac care, orthopedic care, psychiatric care, and the like.

FIG. 5 shows an exemplary comparison of HCPs Hospital A 502 (e.g., HCP-1 from FIG. 4) and Orthopedic Hospital 504 using both a supply mix index calculation 510 and 512 according to certain embodiments of the disclosure and a prior art CMI calculation 506 and 508. The CMI of Hospital A 506 is 0.7740 while the average supply cost based on the CMI for Hospital A 506 is $831. In comparison, the CMI of Hospital B 508 is 2.3228 and the average supply cost based on the CMI for Hospital B 508 is $4,129. Based upon the CMI analysis, Hospital A 502 has a lower adjusted cost of 20% as compared to Hospital B 504. The SMI calculations 510 and 512, however, provide a different outlook on the comparison between Hospital A 502 and Hospital B 504. Specifically, the SMI of Hospital A 510 is 0.1816 while the average supply cost based on the SMI for Hospital A 510 is $3,543. In comparison, the SMI of Hospital B 512 is 4.4852 and the average supply cost based on the SMI for Hospital B 512 is $2,139. Based upon the SMI analysis, Hospital A 502 has a lower adjusted cost of 60% as compared to Hospital B 504.

Figure 6:
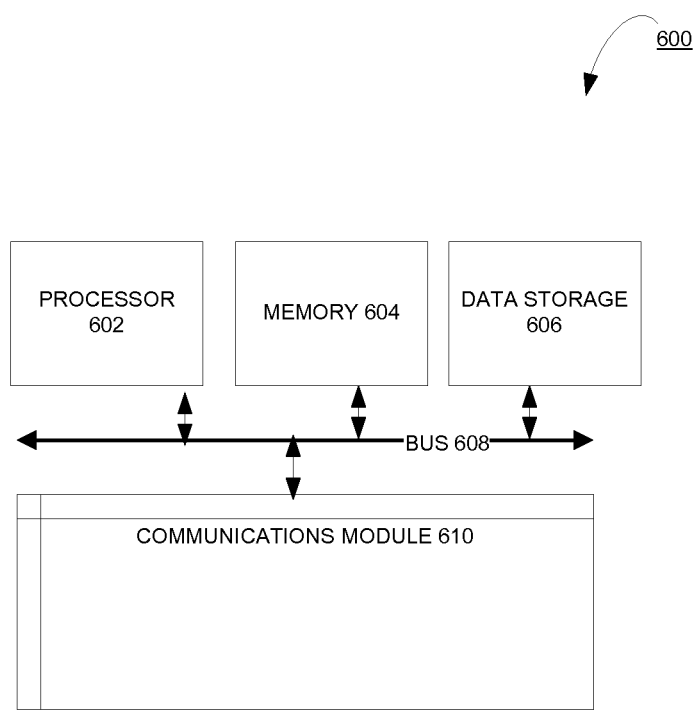
FIG. 6 is a block diagram illustrating an example of a computer system with which the advisor system 110 of FIG. 1 can be implemented.

FIG. 6 is a block diagram illustrating an example of a computer system 600 with which the advisor system 110 of FIG. 1 can be implemented. In certain embodiments, the computer system 600 can be implemented using software, hardware, or a combination of both, either in a dedicated server, or integrated into another entity, or distributed across multiple entities.

Computer system 600 (e.g., advisor system 110) includes a bus 608 or other communication mechanism for communicating information, and a processor 602 (e.g., processor 112) coupled with bus 608 for processing information. By way of example, the computer system 600 can be implemented with one or more processors 602. Processor 602 can be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information. Computer system 600 also includes a memory 604 (e.g., memory 104), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 608 for storing information and instructions to be executed by processor 602. The instructions can be implemented according to any method well known to those of skill in the art, including, but not limited to, computer languages such as data-oriented languages (e.g., SQL, dBase), system languages (e.g., C, Objective-C, C++, Assembly), architectural languages (e.g., Java), and application languages (e.g., PHP, Ruby, Perl, Python). Instructions can also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 604 can also be used for storing temporary variable or other intermediate information during execution of instructions to be executed by processor 602. Computer system 600 further includes a data storage device 606 such as a magnetic disk or optical disk, coupled to bus 608 for storing information and instructions. Computer system 600 can be coupled via communications module 660 (e.g., communications module 116) to various devices (not illustrated). The communications module 610 can be any input/output module. In certain embodiments not illustrated, the communications module 610 is configured to connect to a plurality of devices, such as an input device and/or a display device (e.g., display device 114).

According to one aspect of the present disclosure, the advisor system 110 can be implemented using a computer system 600 in response to processor 602 executing one or more sequences of one or more instructions contained in memory 604. Such instructions can be read into memory 604 from another machine-readable medium, such as data storage device 606. Execution of the sequences of instructions contained in main memory 604 causes processor 602 to perform the process steps described herein. One or more processors in a multi-processing arrangement can also be employed to execute the sequences of instructions contained in memory 604. In alternative embodiments, hard-wired circuitry can be used in place of or in combination with software instructions to implement various embodiments of the present disclosure.

Thus, embodiments of the present disclosure are not limited to any specific combination of hardware circuitry and software.

The term "machine-readable medium" as used herein refers to any medium or media that participates in providing instructions to processor 602 for execution. Such a medium can take many forms, including, but not limited to, non-volatile media, volatile media, and transmission media. Non-volatile media include, for example, optical or magnetic disks, such as data storage device 606. Volatile media include dynamic memory, such as memory 604. Transmission media include coaxial cables, copper wire, and fiber optics, including the wires that comprise bus 608. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read.

Further, a computer readable medium is provided that embodies a computer program, which, when executed on a general purpose computer in the advisor system 110, causes the computer to determine the overall HCP supply mix index ($HCP_{SMI}$) for the particular HCP system 140 and compare (or evaluate) the resource management performance of the particular HCP system 140 to that of the other HCPS 140. The computer program can include a code section (or segment) for each of the steps in FIG. 4, including, e.g., an inpatient volume information receiving code section that receives the inpatient volume information from the HCP system 140, which can include a $DRC_i$ category identifier for each inpatient; a supply mix index retrieving code section that retrieves supply mix index ($SMI_i$) weights from the database 120 (or the local storage in the advisor system 110); a weighted supply mix index value determining code section that determines a weighted supply mix index value for each $DRC_i$ category, by calculating a product of the number of cases $C_i$ of each $DRC_i$ category and the associated supply mix index $SMI_i$ weights (i.e., $C_i \times SMI_i$); an overall HCP supply mix index determining code section that determines an overall HCP supply mix index ($HCP_{SMI}$) for a particular HCP system 140 by summing the products of each of the number of cases $C_j$ with the associated supply mix index weight $SMI_j$ and dividing the result by the total number of cases in the HCP system 140 (i.e., $(\Sigma C_j \times SMI_j)/(\Sigma C_j)$); and an HCP supply mix index comparing code section that compares the HCP supply mix index ($HCP_{SMI}$) for a particular HCP system 140 to that of the other HCPS 140, to determine whether the particular HCP system 140 is performing better than, or worse than various benchmark groups based on the mix of patient cases in the particular HCP system 140.

While the disclosure has been described in terms of exemplary embodiments, those skilled in the art will recognize that the disclosure can be practiced with modifications in the spirit and scope of the appended claims. These examples given above are merely illustrative and are not meant to be an exhaustive list of all possible designs, embodiments, applications or modifications of the disclosure.

What is claimed is:

1. A method for computing, in an advisor system, a plurality of supply cost mix index weights ($SMI_i$s) based on supply cost values associated with multiple health care provider systems (HCPs), the method comprising:

accessing, from a memory in the advisor system, a supply cost value ($SC_i$) associated with each patient case data record from among a plurality of patient case data records stored in the memory, wherein for each patient case data record, the $SC_i$ represents the cost of supplies associated with the patient case data record, wherein each patient case data record is associated with a health care provider system (HCP) of multiple HCPs, wherein each patient case data record is associated with at least one of a plurality of diagnosis related classification values ($DRC_i$s), and wherein i is an index value corresponding to the number of $DRC_i$s;

determining, with a processor in the advisor system, an average supply cost value ($AVG\text{-}SC_i$) associated with each of the $DRC_i$s, each $AVG\text{-}SC_i$ being an average based on the $SC_i$ associated with each of the patient case data records associated with a specific $DRC_i$ and based on the number of patient cases ($C_i$) associated with the specific $DRC_i$;

determining, with the processor in the advisor system, an overall average supply cost value ($SC_{Avg}$), wherein the $SC_{Avg}$ is an overall average based on all of the $SC_i$s from all of the plurality of patient case data records and based on the total number of patient case data records across the multiple HCPs;

determining, with the processor in the advisor system, a supply mix index weight ($SMI_i$) associated with each of the plurality of $DRC_i$s, each $SMI_i$ being determined by dividing the $AVG\text{-}SC_i$ associated with a particular $DRC_i$ by the determined $SC_{Avg}$; and outputting, from the processor in the advisor system, the determined supply mix index weight ($SMI_i$) associated with each of the plurality of $DRC_i$s to a display device connected to the advisor system.

2. The method of claim 1, wherein the supply cost value $SC_i$ associated with each patient case data record includes at least one of a central supply cost value, a pharmacy cost value, and a durable medical equipment cost value.

3. The method of claim 1, wherein for each of the $DRC_i$s, the $AVG\text{-}SC_i$ is determined by generating a sum of the $SC_i$s from each patient case data record that is associated with the $DRC_i$, and then dividing the sum by the corresponding the number of patient cases $C_i$ associated with the $DRC_i$.

4. The method of claim 1, wherein the overall average supply cost value $SC_{Avg}$ is determined by generating a sum of the $SC_i$ from each of the plurality of patient case data records, and then dividing the sum by the total number of patient cases $C_i$ across the multiple HCPs.

5. The method of claim 1, further including the step of:

determining a supply mix index value ($HCP_{SMI}$) for a particular HCP, by generating a sum of the products of each of the number of cases patient $C_j$ with the associated supply mix index weight $SMI_j$, and dividing the result by the total number of cases in the particular HCP system per the formula:

$$HCP_{SMI} = (\Sigma C_j \times SMI_j)/(\Sigma C_j),$$

wherein j represents a subset of i that can range from 1 to n, and further represents a number of $DRC_i$s associated with the particular HCP, and wherein n has a maximum possible value of i.

6. An advisor system for computing a plurality of supply mix index weights ($SMI_i$s) based on supply cost values associated with multiple health care provider systems (HCPs), the system comprising:

a memory for storing a plurality of patient case data records associated with the multiple HCPs, wherein each patient case data record includes at least one supply cost value ($SC_i$) representing a cost of supplies associated with the patient data record and at least one associated diagnosis related classification ($DRC_i$) from a plurality of $DRC_i$s, and wherein i is an index value corresponding to the number of $DRC_i$s; and a processor configured to execute instructions that cause the processor to perform the steps of:

accessing, from the memory, a supply cost value ($SC_i$) associated with each of the plurality of patient case data records and a $DRC_i$ associated with each of the plurality of patient case data records;

determining, an average supply cost value ($AVG\text{-}SC_i$) associated with each of the $DRC_i$s, each $AVG\text{-}SC_i$ being an average based on the $SC_i$ associated with each of the patient case data records associated with a specific $DRC_i$ and based on the number of patient cases ($C_i$) associated with the specific $DRC_i$;

determining an overall average supply cost value ($SC_{Avg}$), wherein the $SC_{Avg}$ is an overall average based on all of the $SC_i$s from all of the plurality of patient case data records and based on the total number of patient case data records across the multiple HCPs;

determining a supply mix index weight ($SMI_i$) associated with each of the plurality of $DRC_i$s, each $SMI_i$ being determined by dividing the $AVG\text{-}SC_i$ associated with a particular $DRC_i$ by the determined $SC_{Avg}$; and outputting the determined supply mix index weight ($SMI_i$) associated with each of the plurality of $DRC_i$s to a display device connected to the advisor system.

7. The system of claim 6, wherein the supply cost value ($SC_i$) associated with each patient case data record includes at least one of a central supply cost value, a pharmacy cost value, and a durable medical equipment cost value.

8. The system of claim 6, wherein for each of the $DRC_i$s the processor determines the $AVG\text{-}SC_i$ by generating a sum of the $SC_i$s associated with each patient case data record associated with the $DRC_i$, and dividing the sum by the corresponding number of patient cases ($C_i$) associated with the $DRC_i$.

9. The system of claim 6, wherein the processor determines the overall average supply cost value $SC_{Avg}$ by generating a sum of the $SC_i$ from each of the plurality of patient case data records and dividing the sum by the total number of patient cases $C_i$ across the multiple HCPs.

10. The system of claim 6, wherein the processor further executes instructions to perform the step of:

determining a supply mix index value ($HCP_{SMI}$) for a particular HCP, by generating a sum of the products of each of the number of cases patient $C_j$ with the associated supply mix index weight $SMI_j$, and dividing the result by the total number of cases in the particular HCP system per the formula:

$$HCP_{SMI} = (\Sigma C_j \times SMI_j)/(\Sigma C_j),$$

wherein j represents a subset of i that can range from 1 to n, and further represents a number of $DRC_i$s associated with the particular HCP, and wherein n has a maximum possible value of i.

11. A non-transitory machine-readable medium comprising machine-readable instructions that, when executed by a processor in an advisor system, cause the processor to execute a method for computing a plurality of supply mix index weights mix index weight ($SMI_i$s) based on supply cost values associated with multiple health care provider systems (HCPs), the method comprising the steps of:

accessing, from a memory, a supply cost value ($SC_i$) associated with each of a plurality of patient case data records stored in the memory, wherein for each patient case data record, the SC represents the cost of supplies associated with the patient data record, wherein each patient case data record is associated with a health care provider system (HCP) of multiple HCPs, wherein each patient case data record is associated with at least one of a plurality of diagnosis related classification values ($DRC_i$s), and wherein i is an index value corresponding to the number of $DRC_i$s;

determining, an average supply cost value ($AVG\text{-}SC_i$) associated with each of the $DRC_i$s, each $AVG\text{-}SC_i$ being an average based on the $SC_i$ associated with each of the patient case data records that are associated with a specific $DRC_i$, and based on the number of patient cases ($C_i$) associated with the specific $DRC_i$;

determining an overall average supply cost value ($SC_{Avg}$), wherein the $SC_{Avg}$ is an overall average based on all of the $SC_i$s from all of the plurality of patient case data records, and based on the total number of patient case data records across the multiple HCPs;

determining a supply mix index weight ($SMI_i$) associated with each of the plurality of $DRC_i$s, each $SMI_i$ being determined by dividing the $AVG\text{-}SC_i$ associated with a particular $DRC_i$ by the determined $SC_{Avg}$; and outputting the determined supply mix index weight ($SMI_i$) associated with each of the plurality of $DRC_i$s to a display device connected to the advisor system.

* * * * *